(12) United States Patent
Barak et al.

(10) Patent No.: US 10,365,231 B2
(45) Date of Patent: Jul. 30, 2019

(54) OPTICAL PHASE MEASUREMENT METHOD AND SYSTEM

(71) Applicant: NOVA MEASURING INSTRUMENTS LTD., Rehovot (IL)

(72) Inventors: Gilad Barak, Rehovot (IL); Dror Shafir, Kiryat Ono (IL); Yanir Hainick, Tel-Aviv (IL); Shahar Gov, Rehovot (IL)

(73) Assignee: NOVA MEASURING INSTRUMENTS LTD., Rehovot (IL)

( * ) Notice: Subject to any disclaimer, the term of this patent is extended or adjusted under 35 U.S.C. 154(b) by 12 days.

(21) Appl. No.: 15/866,768

(22) Filed: Jan. 10, 2018

(65) Prior Publication Data

US 2018/0128753 A1  May 10, 2018

Related U.S. Application Data

(63) Continuation of application No. 14/769,170, filed as application No. PCT/IL2014/050189 on Feb. 20, 2014, now Pat. No. 9,897,553.

(60) Provisional application No. 61/767,364, filed on Feb. 21, 2013.

(51) Int. Cl.
  *G01N 21/956* (2006.01)
  *G03F 7/20* (2006.01)
  *G01N 21/95* (2006.01)

(52) U.S. Cl.
  CPC ....... *G01N 21/956* (2013.01); *G01N 21/9501* (2013.01); *G03F 7/70616* (2013.01); *G03F 7/70625* (2013.01); *G01B 2210/56* (2013.01)

(58) Field of Classification Search
  CPC .............. G01N 21/956; G01N 21/9501; G03F 7/70625; G03F 7/70616; G01B 2201/56
  See application file for complete search history.

(56) References Cited

U.S. PATENT DOCUMENTS

| | | | |
|---|---|---|---|
| 4,744,660 A | 5/1988 | Noguchi et al. | |
| 5,392,118 A | 2/1995 | Wickramasinghe | |
| 5,691,540 A | 11/1997 | Halle et al. | |
| 5,880,838 A | 3/1999 | Marx et al. | |
| 2005/0057755 A1* | 3/2005 | Johnson | G01B 11/0625 438/7 |

(Continued)

FOREIGN PATENT DOCUMENTS

| | | |
|---|---|---|
| CN | 101071058 | 11/2007 |
| CN | 202350735 | 7/2012 |

*Primary Examiner* — Hina F Ayub
(74) *Attorney, Agent, or Firm* — Browdy and Neimark, P.L.L.C.

(57) ABSTRACT

A method and system are presented for use in optical measurements on patterned structures. The method comprises performing a number of optical measurements on a structure with a measurement spot configured to provide detection of light reflected from an illuminating spot at least partially covering at least two different regions of the structure. The measurements include detection of light reflected from said at least part of the at least two different regions comprising interference of at least two complex electric fields reflected from said at least part of the at least two different regions, and being therefore indicative of a phase response of the structure, carrying information about properties of the structure.

17 Claims, 3 Drawing Sheets

(56) References Cited

U.S. PATENT DOCUMENTS

| | | | |
|---|---|---|---|
| 2005/0122515 A1* | 6/2005 | Borden | G01N 21/55 |
| | | | 356/369 |
| 2006/0154156 A1 | 7/2006 | Farah | |
| 2007/0008550 A1 | 1/2007 | Tobiason et al. | |
| 2008/0198367 A1 | 8/2008 | Chang et al. | |
| 2012/0224183 A1 | 9/2012 | Fay et al. | |
| 2013/0059240 A1* | 3/2013 | Van Der Schaar | |
| | | | G03F 7/70633 |
| | | | 430/30 |

* cited by examiner

OPTICAL PHASE MEASUREMENT METHOD AND SYSTEM

TECHNOLOGICAL FIELD AND BACKGROUND

As semiconductor technology progresses, shrinking device dimensions has become an increasingly complex task. Complementing metrology tools, allowing similar improvements in measurement capabilities, are critical for the continual process of this development.

Optical metrology can acquire highly accurate and precise information on the geometry and material properties characterizing patterned structures with small dimensions of the pattern features (critical dimensions). Several physical quantities are commonly measured by optical metrology and in particular by optical critical dimensions (OCD) techniques. For example, optical reflectometry measures the reflection intensity for a broad spectrum, over a single (or small set) of incidence, directions and different polarizations. Ellipsometry allows, in addition, access to information on the relative phase between different polarization states.

Another important attribute of light scattered from a patterned structure is its phase, namely a relative phase between incident and reflected light beams. This phase can be measured using a variety of interferometry techniques. These methods are based on separating the light beam into two parts so that only one part interacts with (is reflected from) the sample. The reflected light is then re-interfered with the second part of the beam ("reference beam"), which did not interact with the sample, and a difference in the optical path length traversed by these two parts is accurately controlled. The interference pattern formed by interference of these two light components in a detection plane is then used to extract the spectral phase.

Existing approaches for measuring phase, including interferometry, are highly delicate, require special measurement apparatus with a reference, and are highly sensitive to environment (e.g. system vibrations). Consequently, such methods are not regularly used for in-line OCD metrology, whereas the more robust methods of reflectometry and ellipsometry are customary.

GENERAL DESCRIPTION

There is a need in the art for a novel approach in optical measurements on patterned structures with small features of the pattern. As indicated above, an important attribute of light reflected/scattered from a patterned structure is its phase, i.e. a relative phase or phase shift between incident and reflected light beams. Such a phase shift is different for interactions of incident light with different regions of the structure (e.g. differently patterned regions, patterned and unpatterned regions, regions with different material layers, etc.).

Further, a phase shift is different for different wavelengths of incident light, and can thus present a spectral phase shift. FIG. 1 schematically illustrates the principles of "spectral phase" effect. As shown, two light beams of different wavelengths $\lambda_1$ and $\lambda_2$ are incident on the same illuminating spot including two different regions of a patterned structure (patterned structure generally could include different patterned and unpatterned regions) and are reflected from these different regions with different phase shifts $\Delta\phi(\lambda_1)$ and $\Delta\phi(\lambda_2)$ respectively. It should however, be understood that when using the single illumination wavelength, $\lambda$, for illuminating two different regions, phase shifts $\Delta\phi_1(\lambda)$ and $\Delta\phi_2(\lambda)$ will be different because of different effects induced by different regions. These phase shifts carry significant information on the properties of the structure. Thus, generally speaking, illumination of two (or more) different regions of a structure causes two (or more) different interactions between incident light and the structure, resulting in different phase shifts being indicative of the properties of the structure.

The present invention provides a novel measurement method and system for optical measurements on patterned structures. The technique of the invention provides a novel approach for measurement of the relative phase between an incident beam and a reflection thereof (i.e. phase response, e.g. spectral phase), and several specific implementations of this capability. This novel approach is as so-called "self-interforometry" approach, based on detection of interference pattern formed by interference of light responses of different regions of the structure to certain illumination (which may be single or multiple wavelengths), and analyzing the detected light to determine the phase shift, to thereby enable extract data about the structure.

This technique can be implemented for various wavelengths and can generate a full spectrum phase differences per wavelength, which is termed here "spectral phase", which can be used as highly valuable information for optical characterization (and importantly for OCD metrology). Specifically, this technique is inherently robust against system vibrations, avoiding the dominant causes for measurement inaccuracies typical of other interferometric systems.

It should be noted that the term "patterned structure" used herein refers actually to a layered structure, where the surface of the structure has different regions. The term "different regions" refers to patterned and unpatterned (homogeneous) regions, and/or regions with different patterns, and/or regions with and without certain layer(s)/film(s) respectively.

It should also be noted that in the description below, the term "measurement spot" refers to detected light, reflected from an illuminating spot on a structure, and carrying measured data. The measurement spot is actually a result of interaction of incident light with the structure within an illuminating spot and a spot (detecting or imaging spot) formed by detected reflection from the illuminated spot on a detector. Accordingly, an optical measurement is performed with a measurement spot which is configured such that a detected spot is formed by light reflections from an illuminating spot, at least partially covering at least different-type regions of a structure.

Thus, according to one broad aspect of the invention, there is provided a method for use in optical measurements on patterned structures. The method comprises performing a number of optical measurements on a structure with a measurement spot configured to provide detection of light reflected from an illuminating spot at least partially covering at least two different regions of the structure; said measurements including detecting light reflected from said at least part of the at least two different regions within the measurement spot, the detected light comprising interference of at least two complex electric fields reflected from said at least part of the at least two different regions, and being therefore indicative of a phase response of the structure, carrying information about properties of the structure.

The illumination includes either normal or oblique incidence mode, or both of them.

Preferably, in order to improve extraction of phase data, more than one measurement is taken with the same measurement spot configuration (e.g. the same-size illuminating spot) but different coverage of the at least two different-type regions of the structure. This enables differential phase measurements.

According to another aspect of the invention, there is provided a system for use in measurements on patterned structures, the system comprising an optical measurement device comprising:

an illumination unit configured and operable for focusing light onto an illuminating spot on a structure at least partially covering at least two different regions of the structure to thereby cause light reflections from said at least two different regions; and a light detection unit collecting light including the light reflections of said at least part of the at least two different regions, the collected light therefore comprising an interference pattern formed by interference of at least two complex electric fields reflected from said at least two different regions, and being therefore indicative of a phase response of the structure, carrying information about properties of the structure.

As indicated above, preferably, at least two optical measurements are taken, with different at least partial coverage of said at least two different regions of the structure. These at least two optical measurements with the different at least partial coverage of the at least two different regions are performed either sequentially, or in parallel (using a position sensitive sensor in the detection unit).

In some embodiments, the measurements are performed with at least two different wavelengths of illumination. In some embodiments, the measurements are performed with multiple wavelengths of illumination, and the detected light is therefore indicative of a spectral phase response of the structure. The detection light may be in the form of a position and wavelength dependent signal.

In some embodiments, the illuminating spot is of a significantly different size than a spot formed by the detected light.

The optical measurement device is typically configured for data communication with a control unit. The control unit is configured and operable for processing data indicative of detected light response and determining relative phase of light reflected from the at least two different regions, thereby enabling determination of properties of the structure.

The control unit may utilize data indicative of mixing coefficients affecting the detected phase response, for the determination of the relative phase. The mixing coefficient may be provided as known data, or may be calculated during the measurements.

For example, at least two optical measurements are performed while shift positions of the measurement spot, thereby controllably modifying values of mixing coefficients affecting the detected light response, and increasing amount of information about the structure in the detected phase responses. Alternatively or additionally, at least two optical measurements are performed with different values of at least one measurement condition, thereby controllably modifying the detected phase response, and increasing amount of information about the structure in the detected phase responses.

In some embodiments, the optical measurement device is configured and operable for separating between TE and TM polarization components in the detected light response.

According to another broad aspect of the invention, there is provided an interferometric method comprising: performing one or more optical measurements comprising: illuminating a structure with an illuminating light spot configured for at least partially covering at least two different-type regions of the structure; and detecting light reflected from the structure and including at least two different light responses of said at least part of the at least two different-type regions, the detected light comprising an interference pattern formed by self interference of at least two complex electric fields reflected from said at least two different regions, and being therefore indicative of a phase response of the structure, carrying information about properties of the structure.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1:
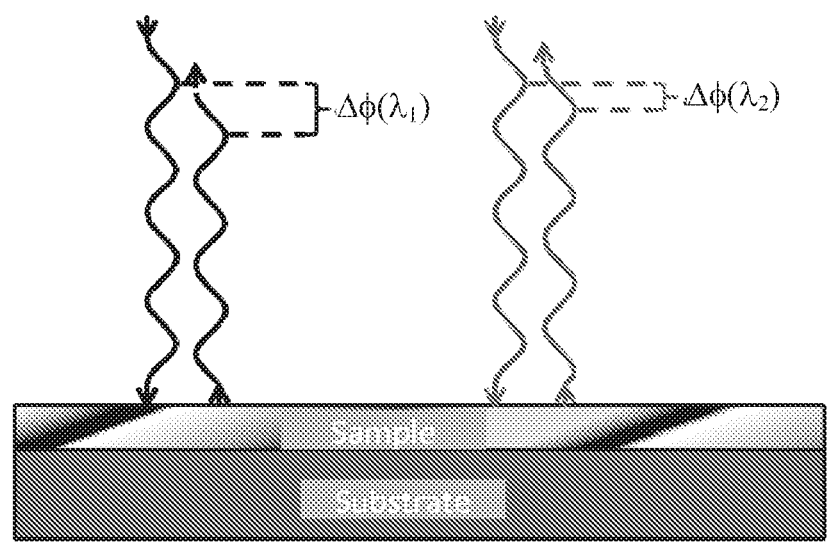
FIG. 1 schematically illustrates interaction of light beams with different wavelengths with a sample, showing different phase shifts of reflections of these beams from the sample.

FIG. 1 described above schematically illustrates an example of interaction of light beams of two different wavelengths with a patterned structure, showing different phase shifts of reflections of these beams from the structure.

The present invention provides a measurement system suitable for measurements (including metrology) on patterned structures, which utilizes interference of light beams returned from different illuminated regions of a structure, enabling robust and accurate phase measurements, e.g. spectral phase measurements. This approach is applicable to structures including large homogeneous (or approximately homogeneous) regions, which is the common case for OCD metrology. The requirement for homogeneity here means that the measured structure in each region is either a periodic structure of largely identical elements (features of a pattern) with a pitch smaller than the optical resolution of the system, or a truly spatially uniform layered stack. Optical resolution of an optical system is known as a diffraction limited spot and is determined as $\lambda/NA$, where $\lambda$ is the wavelength of an illuminating beam and NA is the numerical aperture of the optical system. The specific size and homogeneity conditions are discussed in more detail below.

Figure 2:
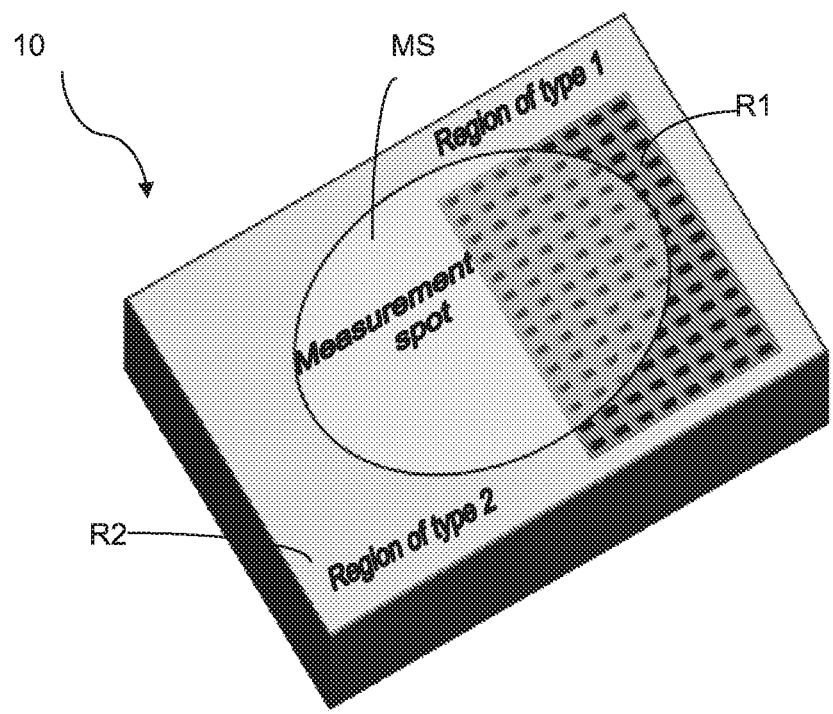
FIG. 2 exemplifies the principles of self-interferometry approach of the invention, where a measurement spot integrates information from a few different-type regions of the sample.

Reference is made to FIG. 2 schematically illustrating the principles of a measurement technique of the present invention. As shown in the figure, a patterned structure 10 has regions of different types, i.e. differently patterned, or patterned and non-patterned regions, or different layered regions. Two such different regions R1 and R2 are shown in this specific not limiting example, where the region of type 1, R1, is a patterned region including a periodic array of repeating structures, and region of type 2, R2, is a uniform periphery surrounding region R1, i.e. R2 is a non-patterned region. An illumination scheme (measurement site and measurement spot configuration) is selected such that an illuminating spot MS covers (at least partially) the two regions R1 and R2 of different types.

It should be understood that the measurements scheme of the present invention is not limited to this specific example, and an illuminating spot may cover more than two regions and thus a measured signal can be collected simultaneously from more than two regions. This is a "self-interferometry" measurement scheme, where the measurement spot integrates information from a few regions of different types. For simplicity, in the following description, the situation where only two regions of different type reside inside the measurement spot will be discussed.

Measured signal, formed by tight components returned (reflected) from different regions, depends on the electric-field response (returned electric-field) from each region, as well as on the relative phase between them. It should be noted that in the description below such light responses are referred as being associated with reflections from the illuminated regions. However, it should be understood that the invention is not limited to specular reflection, and generally not limited to reflection mode at all, and therefore the description in this respect should be interpreted broadly as "light returned/coming from the illuminated region in response to the illumination)".

Thus, in this example, the measured signal depends on the complex electric field $E_1$ reflected from region R1 and the complex electric field $E_2$ reflected from region R2. Common reflectometers and ellipsometers measure the reflected intensities, given by $I=|E|^2$, and consequently cannot access the reflected spectral phase. Indeed, an ellipsometer measures the phase difference between the two polarization components TE and TM, but cannot measure the phase effect or spectral phase effect illustrated in FIG. 1.

When a measurement scheme is configured such that an illuminating spot covers (at least partially) more than one region, the reflectivity or intensity $I_{Tot}$ cannot be simply expressed as a linear combination of the separate reflectivities (intensities), $I_1$ and $I_2$, of the two regions, i.e.

$$I_{Tot} \neq C_1 I_1 + C_2 I_2 \tag{1}$$

This is because the reflected fields from these regions interfere.

In practice, in many cases the measured intensity would be given by $$I_{Tot}(\lambda) = C_1(\lambda)|E_1(\lambda)|^2 + C_2(\lambda)|E_2(\lambda)|^2 + \Re\{C_{12}(\lambda)|E_1(\lambda)||E_2(\lambda)|\exp(i\phi(\lambda))\} \tag{2}$$

In the above equations, $C_1$, $C_2$ and $C_{12}$ are prefactors which determine how the reflected fields are mixed in the measured signal, as will be discussed more specifically further below, and $\phi$ is the phase difference (e.g. spectral phase difference in case plurality wavelengths are used) between the fields reflected from the two different regions.

In this expression, the measured reflectivity is a function of wavelength, and is determined by the reflectivities (light responses) of the two regions ($I_{1,2}$), but importantly also on the interference term, which depends on the spectral phase difference $\phi(\lambda)$, generally on the phase difference due to the different interactions at the different regions.

The measured intensity $I_{Tot}$ holds information on the interference between reflected fields from the different regions. The invention provides a so-called "self-interference" technique, utilizing this dependence of the measured on the interference between reflected fields from the different regions, to extract the phase information, e.g. spectral phase. Thus, the self-interference measurement technique of the present invention utilizes interference between light responses (effects) of different parts of a single sample. It should be noted that the optical system of this self-interference technique does not require an internal reference beam within the system in order to extract the phase. In this respect, this method is inherently different from other interferometry approaches.

As mentioned above, the prefactors $C_1$, $C_2$, and $C_{12}$ determine how the reflected fields are mixed in the measured signal, and as such are termed here is the 'mixing factors'.

It should be noted that the mixing factors can be explicitly calculated, and depend only on the optical system characteristics, such as numerical aperture, main aberrations and illumination scheme (Koehler\critical) and the sample layout including lateral dimensions of the different regions and their layout with respect to the measurement/illuminating spot location. The mixing factors are independent of the details of the specific structure or application within each region independent of details of pattern and/or material composition(s) of layers(s)).

These factors can be a-priori calculated or calibrated independently of the application details. In the following analysis, the mixing factors are assumed to be known.

It should thus be noted that the mixing factor, $C_i$, is a certain function $F_1(\lambda, OS_{charact}, MS_{location})$ of the wavelength $\lambda$, the measurement optics $OS_{charact}$, and the spot location $MS_{location}$, and is independent of structure parameters. In other words, the mixing factors are defined by the configuration of the optical measurement system and measurements conditions, and can thus be predetermined prior to taking actual measurements on the structure with said system and said conditions. The reflected fields $E_1$ and $E_2$ are function $F_2(\lambda, S_{par})$ of the wavelength $\lambda$, and the structure parameters $S_{par}$, but are independent of the spot location: the entire dependence on spot location is encapsulated in how the spot would sum the reflected fields, which is determined by the mixing factors. In addition, the reflected fields depend on the illumination polarization (if illumination is polarized) and on the selected collected polarization (if determined by, e.g., an analyzer). The mixing factors are entirely geometric, and independent of polarization.

The inventors have shown that such decomposition of the measured signal into application- or structure-dependent parts ($E_1$, $E_2$) and optical system and sample layout parts ($C_1$, $C_2$ and $C_{12}$) is valid in cases where the distinct regions are significantly larger than the used wavelength, which is the case for OCD metrology.

The principles of the invention for phase metrology can be implemented with various optical metrology techniques (e.g. spectral reflectometry, spectral ellipsometry). However, the optical system in this case should be appropriately configured to satisfy required conditions for the illumination scheme/channel and in some cases also for the detection channel.

More specifically, for (spectral) phase based measurements, the illumination and detection channels can be configured to provide a desired configuration of a spot size on a structure under measurements. If the mixing factors are to be fund through calculation, it might be beneficial, although not necessary, that either the illumination or collection geometrical spot is very large, and the other small. As standard in the design of optical systems, the geometrical spot sizes are determined by the illumination\collection field stops. One of these spots is commonly required to be small, so that the measured region is limited and confined to the target of interest. However, when the other spot is significantly larger than the coherence length (given by λ/NA), the mixing coefficients $C_1$, $C_2$ and $C_{1,2}$ become much simpler to calculate, and also less sensitive to specific optical attributes and imperfections of the optical system. Similarly, if the mixing factors are to be found through calculation, it might be beneficial, although not necessary, to use Koehler illumination scheme, where a light source is placed at the back focal plane of the illumination channel. Again, this is not a stringent requirement, but would simplify the calculation of the mixing factors and their dependence on some optical attributes of the system. In some embodiments, it might be beneficial to separate and measure reflectivity (light response) of a structure to light of each of the polarization states TE and TM, as these would provide additional information about the structure. For structures which provide significant polarization rotation, measuring the full Jones matrix entries can be additionally beneficial.

With regard to a measurement site, it should be noted that in some embodiments, good knowledge on the measurement location with respect to the structure layout might be preferable, because positioning errors would lead to errors in the assumed mixing factors, and consequently errors in the interpretation of measured data. Consequently, it might be desirable that an imaging channel provides accurate feedback on the measurement spot location.

Further, if the mixing factors are to be found through calculation, the fact that the calculation of the mixing factors is influenced by system aberrations should preferably be taken in account. In this case, low-aberration (high quality) optics can be used, or alternatively these aberrations may be characterized (estimated) and corresponding data be used in the calculation of the mixing factors. The present invention advantageously provides that if the optical system aberrations are well characterized, one can completely account for all system aberrations when calculating the mixing factors (separately from the calculation of the reflected field from the application).

It should be noted that, preferably, the optical measurements include two or more measurements with the same measurement spot (same-size illuminating and detecting spots) applied to the same two or more different regions but with different at least partially coverage of these regions by the illuminating spot. This enables differential phase determination. Such measurements may be applied sequentially, by shifting the measurement spot, or in parallel using 2D sensor in the detection unit.

Figure 3A:
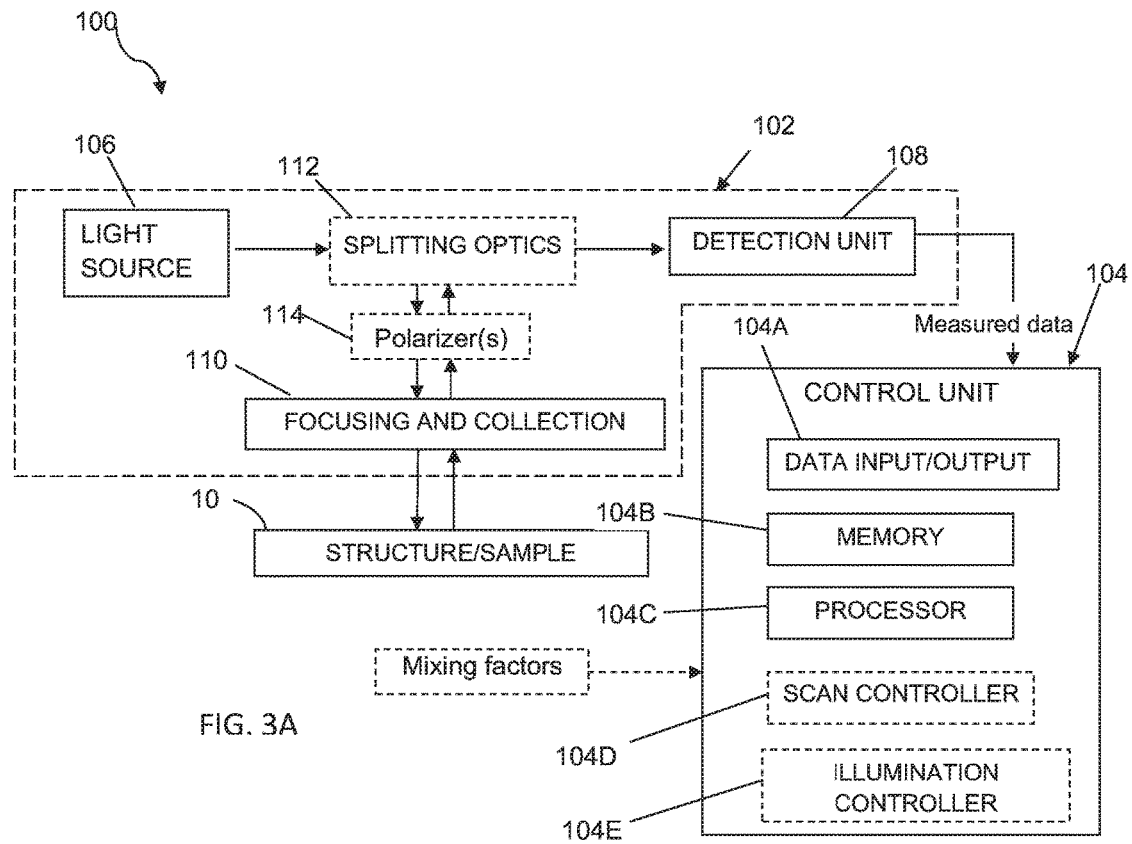
FIG. 3A is a block diagram of a measurement system of the invention.

Reference is made to FIG. 3A showing schematically, by way of a block diagram, a measurement system 100 of the invention. The system 100 includes an optical measurement device 102 connectable (via wires or wireless signal transmission) to a control unit 104. The control unit 104 is typically a computer system including inter alia data input/output utilities 104A, memory utility 104W and processor 104C. In some embodiments, the control unit may also include various controllers for controlling the operation of one or more optical elements of the measurement device, such as a scan controller 104D, and/or illumination controller 104E. The optical measurement device 102 includes a source unit 106, a detection unit 108 and focusing and collection optics 110.

The optical measurement device 102 may be configured for operation with normal incidence in which case the illumination and detection channels are partially overlapping, and accordingly the focusing and collection optics includes optical element(s) located in the common optical path for propagation of illumination light towards a structure and propagation of light returned from a structure 10. Also, in some embodiments, the optical device 102 includes a splitting optics 112. For example in case of the normal incidence configuration, the splitting optics may include a beam splitter/combiner for spatially separating between the illumination and returned light beams. It should be noted that splitting optics 112 may be used (irrespective of normal or oblique configuration of the optical scheme) to perform spectral splitting of light returned from the structure. Further, as described above, the optical device 102 might include polarizer(s) 114.

The control unit 104 receives input measured data indicative of the detected light returned front the measurement spot. The measured data may then be analyzed to detect mixing factors, or as shown in the figure in dashed lines, data indicative of the mixing factors may be supplied as part of the input data (known value of mixing factors). The mixing factors (a priori known or calculated from the preliminary measurements) are then used to interpret measured data and determine the spectral phase.

According to some embodiments of the invention, spectral phase is determined using several measurements taken sequentially at different illuminating spot locations. This, however, imposes limitations on the measurement speed, and therefore might lead to some throughput reduction.

An alternative approach, which is preferable for some applications, such as automatic optical inspection/measurements, is to measure several locations simultaneously. This approach would involve using a 2D sensor where different locations on the sample are simultaneously registered.

Figure 3B:
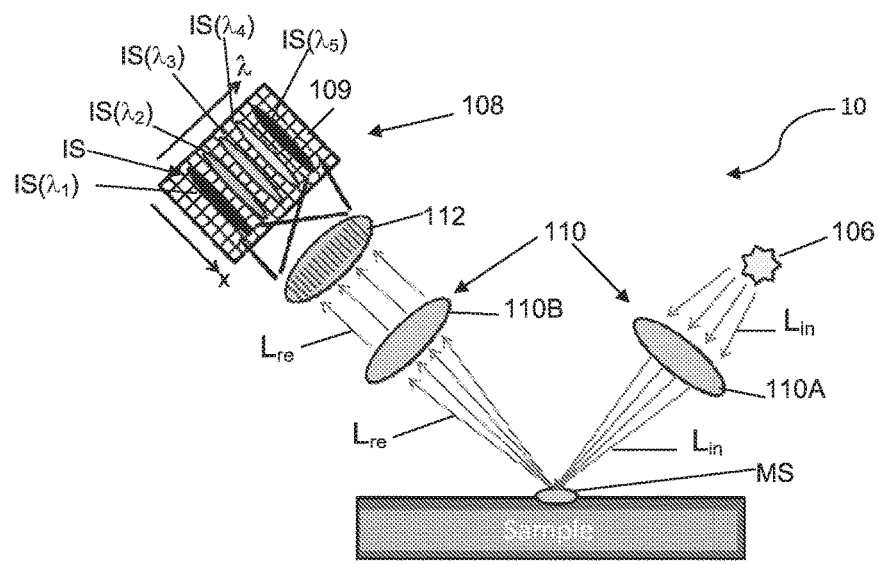
FIG. 3B shows schematically an optical scheme for simultaneous spectral measurements from different spot locations, thus allowing for spectral phase extraction from a single-shot measurement.

An example for an optical measurement device 102 configured with an optical scheme which implements such a single-shot spectral phase measurements is shown in FIG. 3B. In this specific but not limiting example, the optical scheme utilizes oblique incidence. Accordingly, the focusing/collection optics 110 includes separate focusing and collecting lens units 110A and 110B (each including one or more lenses). Light $L_{in}$ from the light source unit 106 is focused onto the structure 10 by objective 110A, creating an illuminated/measurement spot MS. Light $L_{re}$ returned (reflected) from the measurement spot MS is collected by collection objective 110B. Also, in the present example, splitting optics 112 is configured as a spectral splitter, and includes a grating (or prism) to spectrally break the light $L_{re}$ so that different wavelengths are focused on different positions on a 2D sensor 109 of the detection unit 108.

The grating 112 is designed (has a predetermined pattern) such that each wavelength reflected through the grating 112 creates a highly elongated image spot IS on the sensor 109 (in the detection plane), i.e. on one axis (the 'λ' axis) the image spot is highly focused. As shown in the figure, in this example, the grating 112 splits the collected returned light $L_{re}$ into five light components of different wavelengths $\lambda_1$-$\lambda_5$ resulting in respective five image spots IS($\lambda_1$)-IS($\lambda_5$) on the detection surface 109. Hence, along the respective axis, λ-axis in the present example, every pixel line of the 2D sensor 109 "reads" a narrow set of wavelengths but the full spatial span of the measured spot MS in one direction. In the other direction, the 'x' axis in the present example, the grating acts as a lens, imaging the measurement spot MS so that different pixels correspond to spatially distinct regions on the structure. In such a scheme, the detection unit 109 and the splitting optics 112 operate together as a position and wavelength sensitive detector, and a large set of distinct locations on the sample can be captured by a single measurement, allowing efficient spectral phase extraction. It should be noted that such 2D sensors are known for optical spectrometers.

It should be understood that the above-described measurement scheme is a schematic one and can be modified considerably, as long as eventually a position and wavelength dependent signal is obtained. The design can include any set of additional polarizers, retarders or other optical elements. It is also possible to use a normal-incidence design, utilizing a beam-splitter in the illumination and light collection path.

In addition, considering spectral filtering, configuration, a separate lens can be placed before a simple (flat) grating, providing similar position and wavelength sensitive functionality.

Another possibility is not to image the sample onto the 2D detector, but rather to image the back focal plane, so that different reflected directions are mapped to different locations on the 2D sensor. Turning back to FIG. 3B, in this configuration, the x axis would correspond to different reflection directions, and the system allows analysis of the angular dependence of the reflectivity. Such measurement scheme can be implemented, e.g., by using a simple grating which spectrally breaks different wavelengths in one axis ('$\lambda$'), but does not alter the light path in the other axis ("x").

The above-described measurement technique of the invention can be effectively used for OCD. Let us consider such a measurement as described above, providing a mixture of two (or few) unknown fields (Eq. 2). For every wavelength $\lambda$, there are three unknowns, $|E_1|$, $|E_2|$, and their relative phase $\phi$, and one measured quantity $I_{Tot}(\lambda)$. It is possible to increase the amount of available information for example by shifting the measurement spot so as to modify the mixing coefficients $C_i$. Alternatively, some optical parameter(s) of the measurement device can be changed by a known degree (e.g. the illumination\collection numerical aperture), which will also result in a modified measured spectrum. By taking several such measurements, a set of measured spectra $I^i_{Tot}(\lambda)$ is obtained (here i stands for the different spot location\different optical system attributes), each satisfying the following condition:

$$I_{Tot}^i(\lambda) = C_1^i(\lambda)|E_1(\lambda)|^2 + C_2^i(\lambda)|E_2(\lambda)|^2 + \Re\{C_{12}^i(\lambda)|E_1(\lambda)||E_2(\lambda)|\exp(i\phi(\lambda))\}. \quad (3)$$

For each such measurement, the mixing factors can be calculated independently of the application (structure). Consequently, using N such measurements, the values of $|E_1(\lambda)|$, $|E_2(\lambda)|$ and $\phi(\lambda)$ can be directly found, as long as $N \geq 3$ (so that there are at least three equations for these three unknowns). More measurements can be used for noise reduction and accuracy improvements.

Alternatively, if one (or several) of the measured regions is well characterized, so that e.g. $|E_1(\lambda)|$ is known, only two measurements can be used to explicitly extract $|E_2(\lambda)|$ and $\phi(\lambda)$, possibly decreasing the required acquisition time for this measurement.

As stated, this approach pan be expanded to more region types, correspondingly requiring more measurements to allow solution for the different reflectivities and relative (spectral) phases. For example, in the case of three different locations, the measured signal would be expressed as $$I_{Tot}^i(\lambda) = C_1^i(\lambda)|E_1(\lambda)|^2 + C_2^i(\lambda)|E_2(\lambda)|^2 + C_3^i(\lambda)|E_3(\lambda)|^2 + \Re\{C_{12}^i(\lambda)|E_1(\lambda)||E_2(\lambda)|\exp(i\phi_{12}(\lambda))\} + \Re\{C_{23}^i(\lambda)|E_2(\lambda)||E_3(\lambda)|\exp(i\phi_{23}(\lambda))\} + \Re\{(C_{13}^i(\lambda)|E_1(\lambda)||E_3(\lambda)|\exp(i\phi_{13}(\lambda))\}. \quad (4)$$

In this case, there are 6 mixing factors, associated with the contributions of the reflected fields from each of the regions, and the interferences between these fields. Generally, when N region types are simultaneously measured, there would be $N(N+1)/2$ mixing terms.

The reflected spectral phase from a test site holds valuable information on its scattering properties, and can hence be used as basis for optical critical dimensions (OCD) metrology. The relative spectral phases between the different regions can be calculated for any sample using standard techniques for solving electromagnetic reflection problems (e.g. FDTD, RCWA, FEM, eigenmode expansion etc.). Let us consider a sample/structure with known geometry, characterized by a set of unknown parameters. These parameters can be geometrical dimensions, thicknesses and material optical properties (i.e. refractive indices). For any set of values assumed for these parameters, the expected spectral phase (as well as the spectral reflectivity) can be calculated. It should be noted that the spectral phase includes additional information on the measured sample, which is not fully characterized by the spectral reflectivity and/or by the ellipsometric phase.

Given a measured relative spectral phase, it can be compared to a set of pre-calculated such spectral phase. By finding the combination of parameters which produce the best fit between measured and calculated data, the actual parameters of the measured structure can be determined. This approach is customary for OCD metrology, and is commonly applied to the techniques mentioned above. Since in the process of measuring the spectral phase one also obtains the spectral reflectivities $|E_{1,2}|^2$, it is natural and beneficial (although not obligatory) to use both the spectral reflectivity and the spectral phase in such fitting process.

It should be noted that identification of the 'best fit' solution would involve searching for the set of parameters, for which the calculated signature (e.g. spectra, phase spectra) is most similar to the measured. However, considering that the phase and reflectivity information may suffer from different noise attributes, it may be beneficial to weigh these in some nontrivial way. For example, it may be desirable to assign more importance to phase signal than to reflectivity (or vice versa), to have this weight wavelength dependent or to apply any form of nontrivial mathematical manipulation to the data as part of the analysis.

The technique of the present invention allows measurement of test pads with dimensions smaller than the illuminating spot. This capability is highly beneficial for metrology applications, when the illuminating spot is often many tens of micrometers in size, and metrology for regions significantly smaller than this dimension is required. One example for such need is the capability to measure test sites inside the patterned region ('in-die'), where test pads are restricted in their dimensions. Alternatively, such problems arise when the illuminating spot is especially large, for example when highly oblique illumination angles are used.

As explained above, by taking several measurements which mix the contributions from within the test pad and its periphery with different ratios, it is possible to tell apart the separate reflectivities of these two regions. Specifically, it is possible to use this approach to isolate the reflectivity of the pad region, irrespective of its size.

As exemplified above, the surroundings of the region of interest (patterned region R1) are largely homogeneous (non patterned region R2), so that for the different measurement locations only the mixing factors will change, and not the inherent reflectivity. If the pad surroundings are inhomogeneous, errors will be induced in the extracted fields. However, even if the surroundings are not homogeneous, it may be possible to use more measurements to average out the position dependence and accurately extract the reflectivity associated e test pad.

The phase metrology technique of the invention can be used film analysis. Thin film metrology targets accurate measurement of film thicknesses in the range between 0.1 nm and up to a few tens of nm.

Figure 4:
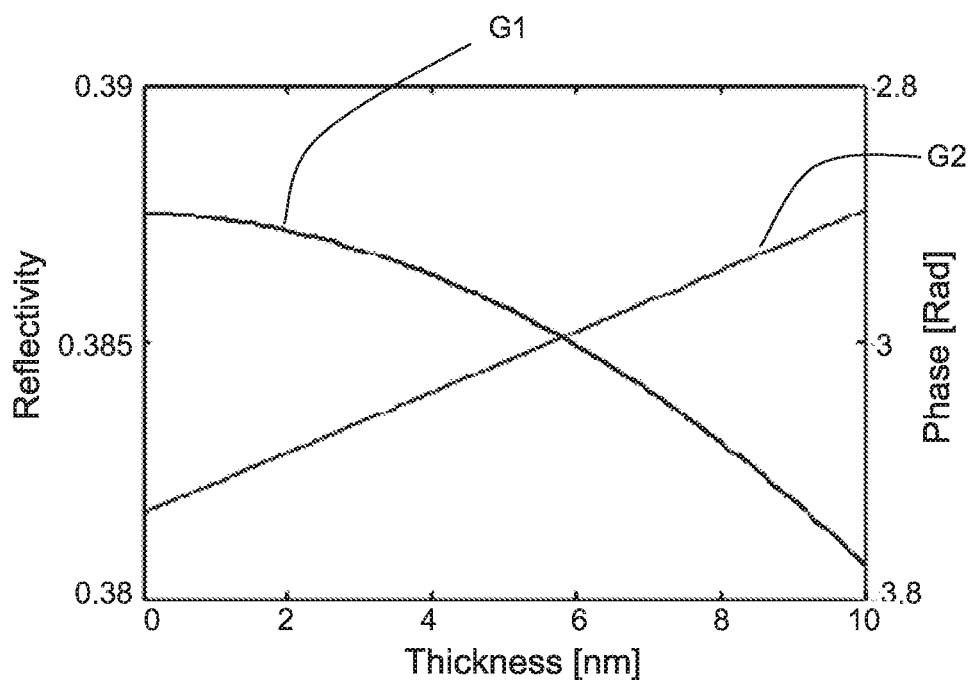
FIG. 4 exemplifies the spectral reflectivity and phase dependence on a film thickness for a structure formed by a thin $SiO_2$ film on top of Si substrate.

In this case, the film reflectivity weakly depends on its thickness, making reflectometry measurements difficult. In contrast, the spectral phase is expected to be highly sensitive to the film thickness, showing (approximately) linear dependence. In this connection, reference is made to FIG. 4, showing spectral reflectivity and phase dependence on film thickness for a specific example of thin $SiO_2$ film on a Si substrate. In the figure, graphs G1 and G2 correspond to the spectral reflectivity and spectral phase, respectively, as a function of the film thickness. For film thickness in the range 0-10 nm, the spectral reflectivity varies by ~1% while the spectral phase varies by ~10% suggesting significantly improved sensitivity.

It should be noted that with the "self interferometry" measurement scheme it might be difficult to properly characterize an extended thin film structure: the measurement spot covers one region holding the thin film, and another region identical to the first but without the thin film. In that case, the phase difference between the two regions will strongly depend on the film thickness. Alternatively a dedicated test regions can be devised to have two regions with different film thicknesses, as is also detailed below.

Typically, optical metrology is applied to test sites comprised of a repeating array of the structure/pattern of interest. This structure (transistor, memory cell etc.) is characterized by multiple geometrical and material properties (thicknesses, dimensions, refractive indices, etc.) which influence the reflected signal. Naturally, the reflected signal is sensitive to all these parameters, while in practice only a small subset of these parameters is of importance to monitor. Moreover, it is often the case that the sensitivity to the parameters of interest is relatively weak compared to sensitivity to irrelevant parameters, imposing stringent requirements on the measurement and modeling accuracy. This sensitivity to irrelevant parameters poses a significant challenge to OCD techniques.

Figure 5:
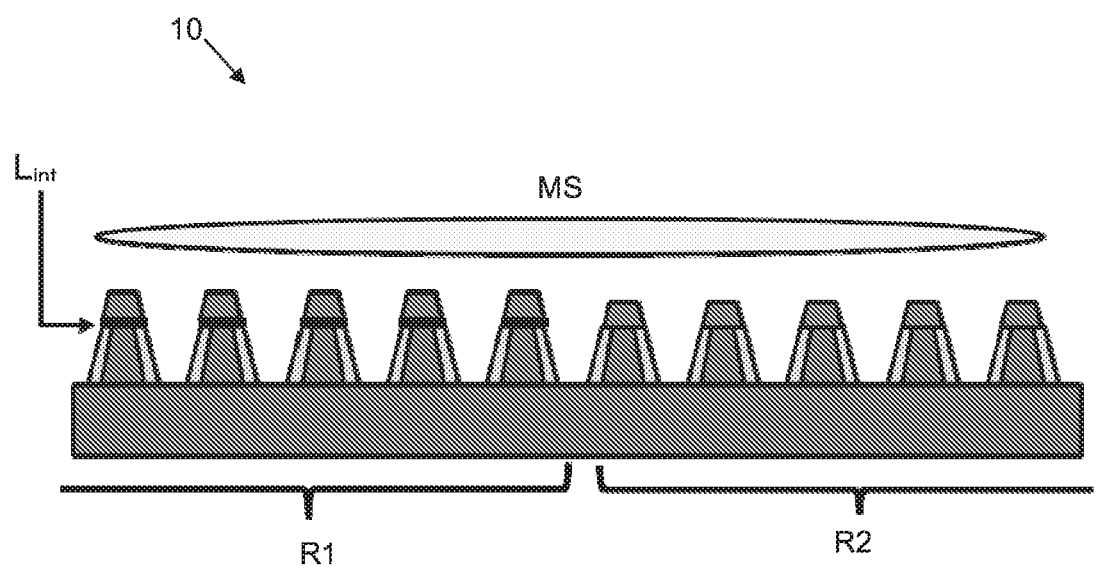
FIG. 5 exemplifies a metrology technique using spectral phase measurements, where the spectral phase difference between two different regions is determined by geometrical and/or material difference between them, and can thus be used as a highly sensitive probe.

The ability to measure the relative phase between different regions allows for a unique kind of metrology approach. In this connection, reference is made to FIG. 5 exemplifying a specifically designed test pad/structure 10, with two different regions R1 and R2, which are both patterned but with different patterns. In this specific not limiting example, region R1 holds one pattern, while region R2 (termed a "reference region") holds a similar pattern as region R1, hut with some modification introduced to the parameter(s) of interest. In this example, the parameter of interest is the thickness of some internal layer $L_{int}$, which exists in the pattern of region R1 while is removed the pattern in the reference region R2. An illuminating spot MS covers regions R1 and R2 and thus a light response from the illuminating spot integrates the reflected fields from both regions, allowing for spectral phase extraction using the technique of the to invention described above. While the reflected spectrum is determined by the entire structure, the spectral phase difference between the two regions R1 and R2 is highly sensitive to the difference between them (specifically, if no such modification is introduced, the spectral phase difference would be 0).

This approach can be applied to various metrology reflectometry methods, e.g. spectral reflectometry and spectral ellipsometry addition, it can be applied for the characterization of (essentially) any parameter of interest of a patterned structure, e.g. CD, pitch, material properties, side-wall angle etc.

It is similarly possible to change more than one parameter of the structure in the two regions, in which case the spectral phase difference will be sensitive primarily to those parameters which were modified. Furthermore, it is possible to design a test pad comprised of more than two such regions, possibly allowing improved differentiation between different parameters of interest.

As evident from Eq. 2 above, the ability to separate system-related from application dependent contributions to the measures signal, i.e. light response, allows a unique approach for characterization of the optical measurement system. By measuring a well characterized structure, with specific spatial (or angular) reflectivity properties (e.g. a knife-edge sample), the obtained (measured) and expected (modeled) signals can be compared. Any difference between the measured and expected signals is inevitably related to the optical system characteristics, for example its aberrations.

Since the influence of the optical system characteristics and aberrations can be directly used to derive the expected mixing parameters, it is furthermore possible to look for a set of aberrations which affect the measured signal. This can be accomplished by a variety of fitting methods. For example, it is possible to calculate the mixing factors expected for a variety of system aberrations, and identify the combination of aberrations which provides a best fit for the measurement. Alternatively, regression techniques could be used.

Another possible implementation is to measure the same location on the same sample through two different optical configurations (e.g. different objectives). The differences between the measured, signals can be related to the differences in optical characteristics, as discussed above, Similarly, several measurements can be taken at different polarizations, enabling polarization-dependent characterization of the elements. Such analysis could be useful, for example, for the characterization of stress effects (which is known to cause birefringence, i.e. polarization-dependent transmission).

More generally, such analysis can be done for any parameter of the optical system which could be varied. As exemplified above, measurement can be done for multiple wavelength and obtain a wavelength-dependent characterization. Alternatively, or additionally, the location and\or orientation of some optical element can be varied, and the optical system can be characterized for varying placements of the optical element(s). Such characterization can then be used to optimize the system to any desired attributes.

Thus, the present invention provides a simple and effective technique for characterizing/measuring patterned structures. To this end, the invented technique utilizes simultaneous optical measurement on a portion of the structure including two different regions, and determining the spectral phase of the light response from the structure. Measured data indicative of the light response from two different regions (e.g. measured intensity) holds information on the interference between returned (reflected) fields from the different regions, and this dependence is used to extract the spectral phase.

The invention claimed is:

1. A method for use in optical measurements on patterned structures to determine parameters of a region of interest in the structure, the method comprising:
performing at least two optical measurements on the structure, wherein each of said at least two optical measurement comprises illuminating the region of interest with an illuminating spot of a size larger than said region of interest, detecting reflected light fields reflected from the illuminating spot, and generating measured data corresponding to the detected reflected light fields, said measured data being indicative of mixed contributions of reflected light fields from illuminated region of interest and from illuminated different region in surroundings of the region of interest, and wherein said at least two optical measurements are performed with at least one different measurement condition such that the at least two measured data are indicative of differently mixed contributions of the reflected light fields from the illuminated region of interest and the illuminated different region; and
processing the at least two measured data and extracting data indicative of the reflected light field from the illuminated region of interest, thereby enabling determination of the parameters of the region of interest.

2. The method according to claim 1, wherein said region of interest and said different region in the surrounding of the region of interest are first and second patterned regions having different first and second patterns, respectively.

3. The method according to claim 1, wherein one of said region of interest and said different region in the surrounding of the region of interest is a patterned region and the other of said region of interest and said different region is an unpatterned region.

4. The method according to claim 1, wherein said region of interest is a patterned region.

5. The method according to claim 1, wherein said number of the optical measurements are performed with at least one normal and oblique incidence modes.

6. The method according to claim 1, wherein said at least one different measurement condition comprise illumination with different wavelengths.

7. The method according to claim 1, wherein each of said optical measurements are performed with multiple wavelengths, the detected light being therefore indicative of a spectral response of the structure.

8. The method according to claim 1, wherein said processing of the at least two measured data utilizes data indicative of mixing coefficients.

9. The method according to claim 8, wherein the mixing coefficients are determined from preliminary measurements on the structure.

10. The method according to claim 8, wherein said at least two optical measurements comprise optical measurements performed with shifted positions of the illuminating spot, thereby controllably modifying values of the mixing coefficients affecting the detected reflected light fields, and increasing amount of information about parameters of the region of interest.

11. A system for use in measurements on patterned structures to determine parameters of a region of interest in the structure, the system comprising:
an optical measurement device comprising:
an illumination unit configured and operable for focusing light onto the structure with an illuminating spot of a size larger than a region of interest being measured to thereby cause light reflections from illuminated region of interest under measurements and illuminated different region in surrounding of said region of interest; and
a light detection unit collecting light including the light reflections from the illuminated region of interest and the illuminated different region in surrounding of the region of interest, and generating measured data corresponding to the collected light, the measured data being therefore indicative of mixed contributions of the reflected light from the illuminated patterned region and from the illuminated different region in surrounding of the region of interest; and
a control unit configured for data communication with the measurement device, said control unit being configured and operable to process at least two measured data corresponding to at least two optical measurements differing in at least one measurement condition and extract data indicative of the reflected light from the illuminated region of interest, to thereby enable determination of the parameters of the region of interest.

12. The system according to claim 11, wherein the optical measurement device is configured to perform optical measurements with at least one normal and oblique incidence modes.

13. The system according to claim 11, wherein the optical measurement device is configured and operable to perform optical measurements using illumination with different wavelengths.

14. The system according to claim 11, wherein the optical measurement device is configured and operable to perform two or more optical measurements, each with multiple wavelengths, the detected light being therefore indicative of a spectral response of the structure.

15. The system according to claim 11, wherein the control unit is configured to perform said processing of the at least two measured data utilizing data indicative of mixing coefficients.

16. The system according to claim 15, wherein the control unit is configured to access stored data about the mixing coefficients determined from preliminary measurements on the structure.

17. The system according to claim 15, wherein the optical measurement device is configured and operable to perform optical measurements with shifted positions of the illuminating spot, thereby controllably modifying values of the mixing coefficients affecting the detected reflected light fields, and increasing amount of information about parameters of the region of interest.

* * * * *